(12) United States Patent  (10) Patent No.: US 8,319,506 B2
Liu et al.  (45) Date of Patent: Nov. 27, 2012

(54) DETECTOR STATE MONITORING SYSTEM AND A PORTABLE DETECTOR INCLUDING SAME

(75) Inventors: James Zhengshe Liu, Glendale, IL (US); Scott Petrick, Sussex, WI (US); Donald Langler, Brookfield, WI (US); Chuande Liu, Waukesha, WI (US); Gary McBroom, Dousman, WI (US); Roy Schley, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 3 days.

(21) Appl. No.: 12/824,601

(22) Filed: Jun. 28, 2010

(65) Prior Publication Data

US 2011/0316568 A1 Dec. 29, 2011

(51) Int. Cl.
*G01R 27/08* (2006.01)
*H05G 1/64* (2006.01)
(52) U.S. Cl. ........................ 324/691; 378/98.8
(58) Field of Classification Search .......................... None
See application file for complete search history.

(56) References Cited

U.S. PATENT DOCUMENTS

| 5,877,501 | A | * | 3/1999 | Ivan et al. ................. 250/370.09 |
| 7,016,467 | B2 | | 3/2006 | Brooks |
| 7,289,602 | B1 | * | 10/2007 | Polichar et al. .............. 378/98.8 |
| 7,359,482 | B2 | | 4/2008 | Schmitt |
| 7,997,798 | B2 | * | 8/2011 | Liu et al. ........................ 378/198 |
| 2007/0140424 | A1 | * | 6/2007 | Serceki ........................... 378/62 |
| 2008/0240358 | A1 | | 10/2008 | Utschig et al. |
| 2008/0292062 | A1 | | 11/2008 | Marar |
| 2009/0028295 | A1 | | 1/2009 | Ohta et al. |
| 2011/0254563 | A1 | * | 10/2011 | Liu et al. ....................... 324/538 |

* cited by examiner

*Primary Examiner* — Vinh Nguyen

(74) *Attorney, Agent, or Firm* — The Small Patent Law Group; Dean D. Small

(57) ABSTRACT

A portable imaging detector and a method for operating the portable imaging detector are provided. The portable imaging detector includes a docking connector having a plurality of docking connector contacts. The method includes measuring a voltage at a first docking connector contact, and determining whether the portable detector is (i) operating in a digital cassette mode or is (ii) installed in either a cassette holder or a charging bin using the measured voltage. A detector state monitoring system is also discussed.

19 Claims, 9 Drawing Sheets

DETECTOR STATE MONITORING SYSTEM AND A PORTABLE DETECTOR INCLUDING SAME

BACKGROUND OF THE INVENTION

The subject matter disclosed herein relates generally to imaging detectors, and more particularly, to a device for determining a state of a portable imaging detector.

Portable detectors may be used in both mobile and fixed state applications. For example, when the portable detector is operated in a mobile state, a battery housed within the portable detector is used to power the portable detector. In a fixed state, the portable detector is coupled, or "docked" to an imaging system. More specifically, the portable detector includes a docking connector that mates with a connector that is part of the imaging system. The combination of the connector on the portable detector and the imaging system connector enables the portable detector to receive power from, and communicate with, the imaging system workstation via cables that are part of the imaging system.

It is preferable to operate the portable detector in the wireless mode to enable the operator to take full advantage of the capabilities of the portable detector. In the wireless mode, imaging information is transmitted wirelessly from the portable detector to the imaging system. However, when the portable detector is used to perform complex imaging procedures, the quantity of imaging information transmitted wirelessly from the portable imaging detector may be sufficient to cause a reduction in the overall operational speed of the imaging system, thus increasing the amount of time required to generate an image.

BRIEF DESCRIPTION OF THE INVENTION

In one embodiment, a method of operating a portable imaging detector is provided. The portable imaging detector includes a docking connector having a plurality of docking connector contacts. The method includes measuring a resistance between two of the docking connector contacts, and determining whether the portable detector is (i) operating in a fixed state because it is installed in a cassette holder or is (ii) operating in a portable state either as a digital cassette or being charged in a charging bin.

In another embodiment, a detector state monitoring system is provided. The detector state monitoring system includes a docking connector coupled to a portable imaging detector and a processor coupled to the docking connector. The processor is programmed to determine when the portable detector is in a portable state or a fixed state, and when the portable detector is determined to be in the portable state, the processor is further programmed to determine if the portable detector is operating in a digital cassette or installed in a charging bin.

In a further embodiment, a portable x-ray detector is provided. The portable x-ray detector includes a detector panel including a plurality of detector elements and a detector state monitoring system coupled to the detector panel. The detector state monitoring system includes a docking connector and a processor coupled to the docking connector. The processor is programmed to determine when the portable detector is in a portable state or a fixed state, and when the portable detector is determined to be in the portable state, the processor is further programmed to determine if the portable detector is installed in a charging bin.

In a still further embodiment, a portable x-ray detector is provided. The portable x-ray detector includes a detector panel including a plurality of detector elements and a detector state monitoring system coupled to the detector panel. The detector state monitoring system includes a docking connector and a processor coupled to the docking connector. The processor is programmed to determine when the portable detector is in operating in a wireless mode of operation, and automatically transition the portable detector from a first power consumption mode to a second power consumption mode based on the determination.

DETAILED DESCRIPTION OF THE INVENTION

Figure 1:
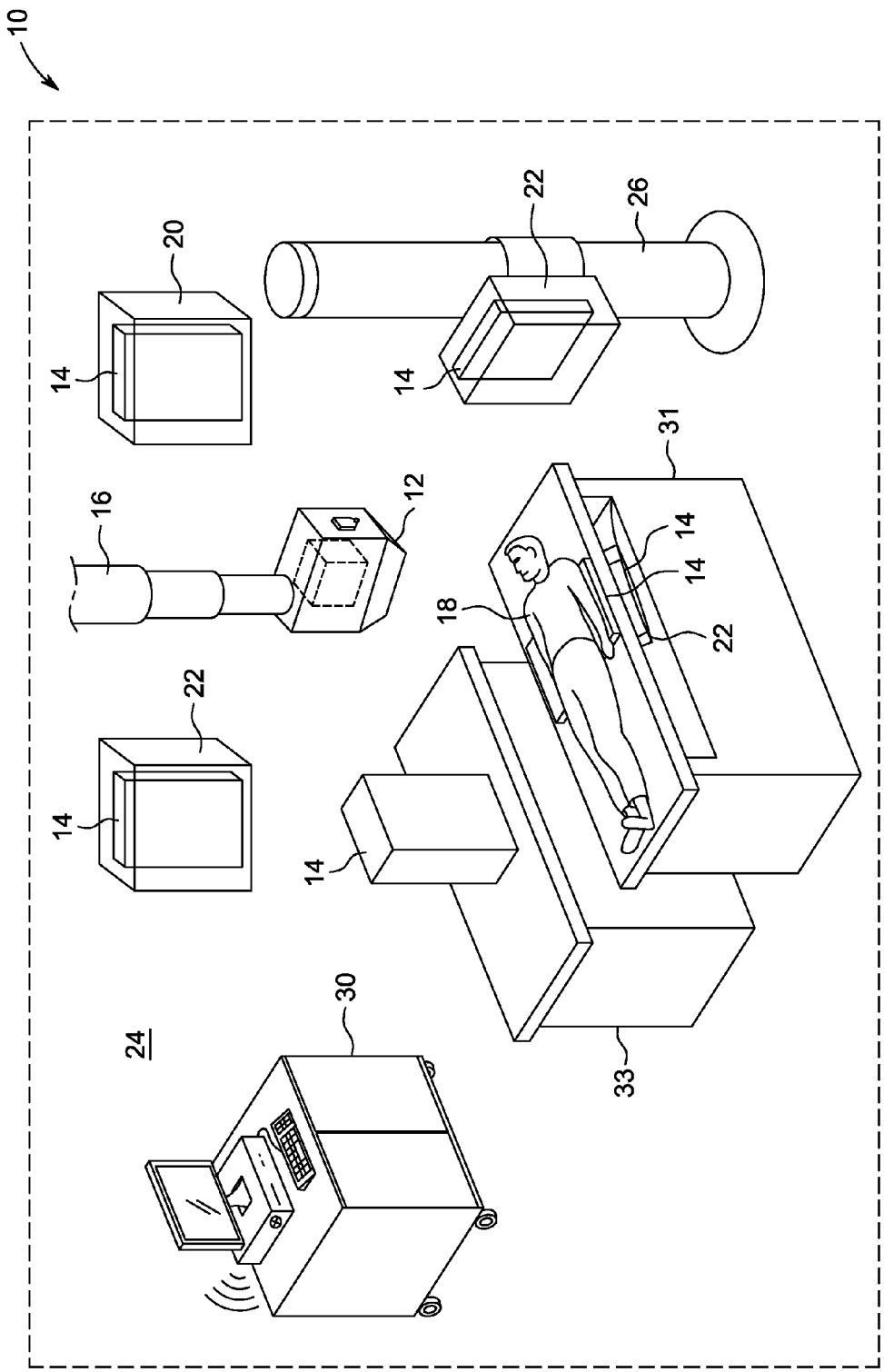
FIG. 1 is a pictorial view of an exemplary medical imaging system formed in accordance with various embodiments.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or in multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate, or are configured to generate, at least one viewable image.

Figure 2:
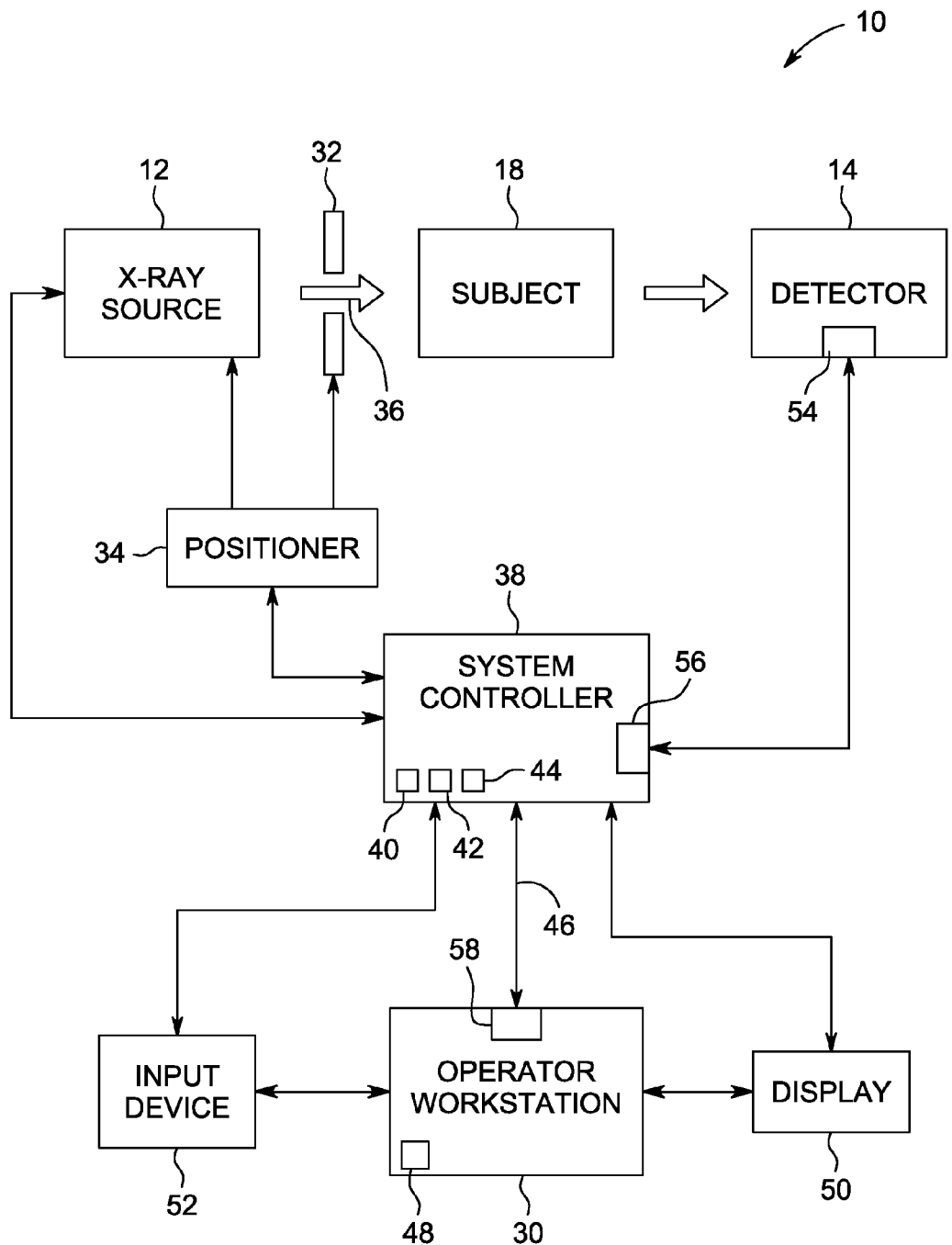
FIG. 2 is a block schematic diagram of the exemplary medical imaging system shown in FIG. 1 in accordance with various embodiments.

Referring to the drawings, FIG. 1 is a pictorial view of an exemplary imaging system 10 formed in accordance with an embodiment of the present invention. FIG. 2 is a block schematic diagram of the exemplary imaging system 10 shown in FIG. 1. Various embodiments of the invention may be used with the exemplary medical imaging system 10 as shown in FIG. 1. The medical imaging system 10 may be any type imaging system such as, for example, an x-ray imaging system or a tomosynthesis imaging system. Moreover, the various embodiments are not limited to medical imaging systems for imaging human subjects, but may include veterinary or non-medical systems for imaging non-human objects, or non-destructive testing systems (e.g. airport baggage systems) etc.

The medical imaging system 10 in the preferred embodiment is a digital radiography imaging system 10 that includes an x-ray source 12 and at least one detector 14. In the exemplary embodiment, the detector 14 is a portable x-ray detector. As shown in FIG. 1, the detector 14 may be utilized in various locations and applications, and in either a fixed state or a portable state. The x-ray source 12 is mounted to a gantry 16. The gantry 16 may be movable to enable the x-ray source 12 to be properly positioned with respect to a subject 18 being imaged or to enable the x-ray source 12 to be moved from one imaging room to another. Optionally, the gantry 16 may be stationarily mounted by coupling the gantry to a floor or ceiling, for example.

The detector 14 may be operated in a fixed state or a portable state. In one mode of operation, when the detector 14 is operated in the fixed state, the detector 14 is installed in a cassette holder 22. The cassette holder 22 may also be referred to herein as a bucky. The cassette holder 22 is mounted or attached to a fixed location. For example, as shown in FIG. 1, the cassette holder 22 may be coupled to a wall 24 or a post 26. When the cassette holder 22 is coupled to the wall 24 or the post 26, the cassette holder 22 is often referred to as a wall bucky. Moreover, the cassette holder 22 may fixedly installed in an imaging table 31. When installed in the imaging table 31, the cassette holder 22 may be referred to as a table bucky. In the fixed state, the detector 14 receives power from the cassette holder 22. Moreover, the cassette holder 22 also enables the x-ray detector to communicate with an imaging workstation, such as an imaging workstation 30. During operation, information is transmitted from the workstation 30 to the detector 14 via wires (such as an Ethernet cable) in the cassette holder 22. Additionally, information generated by the detector 14 may be transmitted to the workstation 30 via wires (such as an Ethernet cable) in the cassette holder 22. The information that is generated and transferred may be at a rate higher than a wireless connection can support. Accordingly, in the fixed state, the detector 14 is mounted in a fixed position to the cassette holder 22 and power and communication signals are transmitted from, and received by the detector 14 via the cassette holder 22.

In another mode of operation, the detector 14 is operated in the portable state. For example, in the portable state, the detector 14 is installed into a charging bin 20. The charging bin 20 is configured to provide power to the detector 14 to charge a battery (not shown) installed in the detector 14, but does not provide a wired communication path between the detector 14 and the imaging workstation 30. In another portable state, the detector 14 receives operational power from the battery installed in the detector 14. This portable state is also referred to herein as digital cassette mode. Additionally, operational and communication signals are transmitted wirelessly between the detector 14 and the workstation 30. For example, as shown in FIG. 1, in the portable state, the detector 14 may be positioned on a table 31 beneath the subject 18. The detector 14 may also be positioned on a separate table 33 that is adjacent to the subject 18. Accordingly, in the portable state, the detector 14 is not coupled to the cassette holder 22.

Referring to FIG. 2, the imaging system 10 may also include a collimator 32 that is disposed between the x-ray source 12 and the subject 18. The imaging system 10 may also include a positioner 34. The positioner 34 is a mechanical controller coupled to the x-ray source 12 and the collimator 32 for controlling the positioning of the x-ray source 12 and the collimator 32. During operation, the imaging system 10 generates images of the subject 18 by means of an x-ray beam 36 emitted by the x-ray source 12, and passing through the collimator 32. The collimator 32 forms and confines the x-ray beam 36 to a desired region, wherein the subject 18, such as a human patient, an animal or an object, is positioned. A portion of the x-ray beam 36 passes through or around the subject 18 and, being altered by attenuation and/or absorption by tissues within the subject 18, continues on toward and impacts the detector 14. The detector 14 converts x-ray photons received on its surface to lower energy light photons, and subsequently to electric signals, which are acquired and processed to reconstruct an image of internal anatomy of the subject 18.

The imaging system 10 further includes a system controller 38 coupled to the x-ray source 12, the detector 14, and the positioner 34 for controlling operation of the x-ray source 12, the detector 14, and the positioner 34. It should be realized that the system controller 38 is configured to transmit and receive information from the detector 14, the detector 14 is manually positioned by the operator, when the detector is operated as a digital cassette, or when the operator places the detector in a cassette holder. The system controller 38 may supply both power and control signals for imaging examination sequences when the detector is operated in the fixed state. In general, the system controller 38 controls the operation of the imaging system 10 to execute examination protocols and to process acquired image data. The system controller 38 may also include signal processing circuitry, based on a general purpose or application-specific computer, associated memory circuitry for storing programs and routines executed by the computer, as well as configuration parameters and image data, interface circuits, and so forth.

The system controller 38 may further include at least one computer or processor 40 that is configured to coordinate the operation of the x-ray source 12, the detector 14, and the positioner 34, and to process image data acquired from the detector 14. As used herein, the term "computer" or "processor" may include any processor or processor-based system including systems using controllers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer". During operation, the processor 40 carries out various functions in accordance with routines stored in an associated memory circuitry 42. The associated memory circuitry 42 may also store configuration parameters, imaging protocols, operational logs, raw and/or processed image data, and so forth.

The system controller 38 may further include interface circuitry 44 that permits an operator or user to define imaging protocols, imaging sequences, determine the operational status and health of system components, and so-forth. The interface circuitry 44 may allow external devices to receive images and image data, and command operation of the radiography system, configure parameters of the system, and so forth. The system controller 38 may be coupled to a range of external devices via a communications interface. Such devices may include, for example, the operator workstation 30 for interacting with the system controller 38 or directly with the detector 14, processing or reprocessing images, viewing images, and so forth.

The operator workstation 30 may be embodied as a personal computer (PC) that is positioned near the imaging system 10 and hard-wired to the system controller 38 via a communication link 46. The workstation 30 may also be embodied as a portable computer such as a laptop computer or a hand-held computer that transmits information to the system controller 38. In one embodiment, the communication link 46 may be hardwired between the system controller 38 and the workstation 30. Optionally, the communication link 46 may be a wireless communication link that enables information to be transmitted to or from the workstation 30 to the system controller 38 wirelessly. In the exemplary embodiment, the workstation 30 controls real-time operation of the imaging system 10. The workstation 30 is also programmed to perform medical image diagnostic acquisition and reconstruction processes described herein.

The operator workstation 30 includes a central processing unit (CPU) or computer 48, a display 50 and an input device 52. In operation, the computer 48 executes a set of instructions that are stored in one or more storage elements or memories, in order to process input data. The storage elements may also store data or other information as desired or needed. The storage elements may be in the form of an information source or a physical memory element within the computer 48. The set of instructions may include various commands that instruct the processor 48 as a processing machine to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

The CPU 48 receives inputs, e.g., user commands, from the input device 52. The input device 52 may be, for example, a keyboard, a mouse, a touch-screen panel, and/or a voice recognition system, etc. Through input device 52 and associated control panel switches, the operator can control the operation of the imaging system 10 and the positioning of the x-ray source 12 for a scan. Similarly, the operator can control the display of the resulting image on the display 50 and can perform image-enhancement functions using programs executed by the workstation CPU 48. The workstation 30 may also be linked to the system controller 38 by one or more network links.

In the exemplary embodiment, to transmit the information from the detector 14 to the system controller 38 or the workstation 30, when the detector 14 is operating in the portable state, the detector 14 includes a transceiver 54. The transceiver 54 enables the detector information to be transmitted wirelessly to a corresponding transceiver 56 that is mounted in the system controller 38. Optionally, the transceiver 54 is configured to transmit the detector information in a wireless format to a corresponding transceiver 58 that is mounted in the workstation 30.

Figure 3:
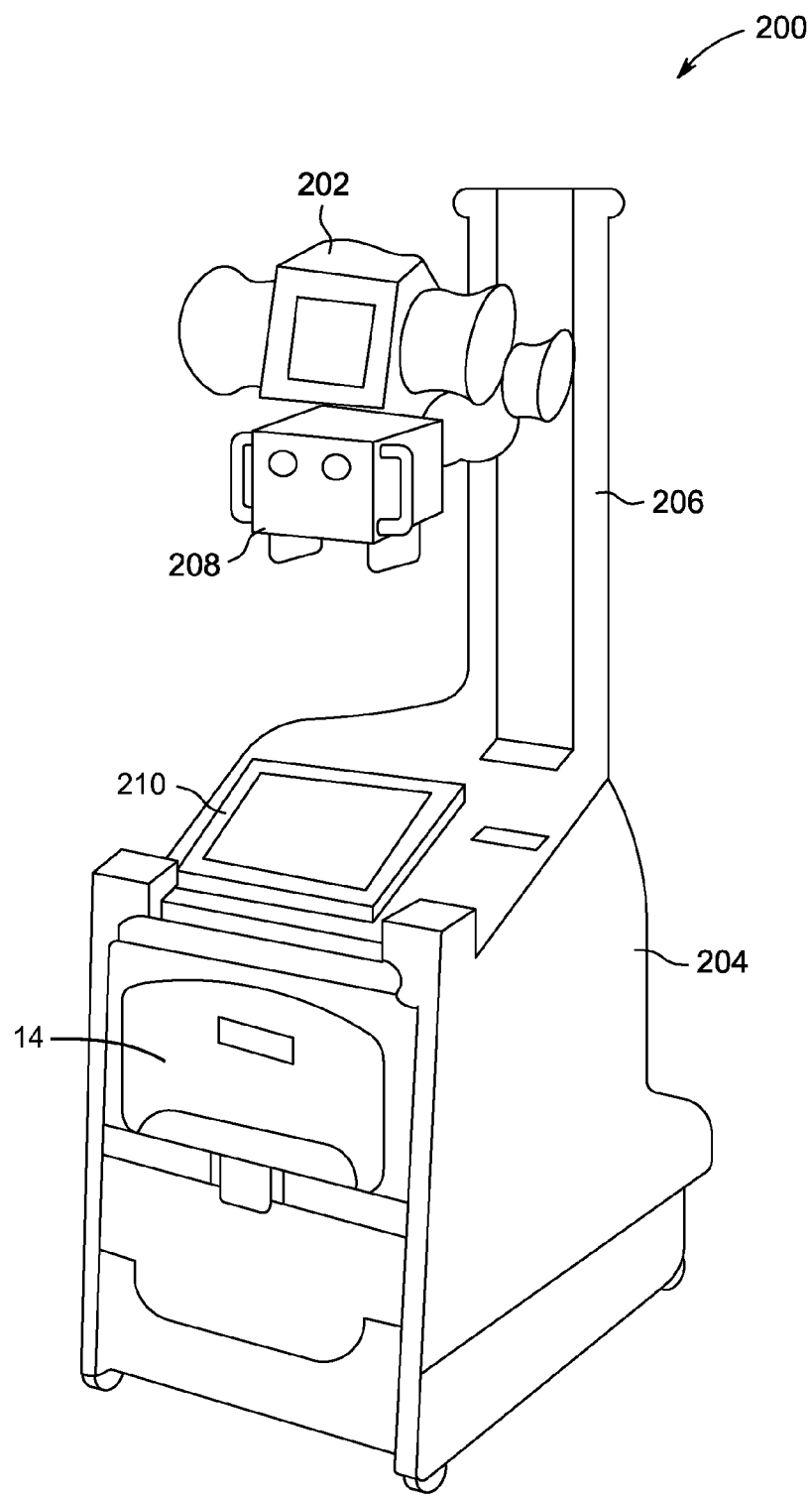
FIG. 3 is a perspective view of another exemplary medical imaging system in accordance with various embodiments.

FIG. 3 is a perspective view of another exemplary medical imaging system 200 in accordance with various embodiments. The medical imaging system 200 in the preferred embodiment is a digital radiography imaging system that includes an x-ray source 202 and at least one detector 14 that is shown stored in a compartment forming a portion of the medical imaging system 200. The detector 14 may be removed from the compartment and operated in a digital cassette mode by placing the detector 14 on the table 33 for example. Additionally, the detector 14 may be installed in the charging bin 20 or in various other locations shown in FIG. 1. In the exemplary embodiment, the detector 14 is a portable x-ray detector. As shown in FIG. 3, the detector 14 is preferably mounted to a portable workstation 204 to enable the medical imaging system 200 to be utilized in various locations and applications. The x-ray source 202 is mounted to a portable gantry 206. The gantry 206 may be movable to enable the x-ray source 202 and the detector 14 to be properly positioned with respect to a subject (not shown) being imaged. The medical imaging system 200 also includes a display 210. The display 210 enables the operator to control the display of the resulting image and can perform image-enhancement functions using programs executed by the medical imaging system 200. During operation, the imaging system 200 enables the x-ray source 202 and the detector 14 to be moved from one imaging room to another.

In the exemplary embodiment, the imaging system 200 may also include a collimator 208 that is disposed between the x-ray source 202 and the subject. The imaging system 200 may also include a system controller (not shown) that is substantially similar to the system controller 38 shown in FIG. 2. In operation the imaging system 200 system controller operates in a similar manner to the system controller 38. For example, the imaging system 200 system controller may includes a computer to coordinate the operation of the x-ray source 202 and the detector 14, and to process image data acquired from the detector 14. The imaging system 200 system controller 38 may further include interface circuitry (not shown) that permits an operator or user to define imaging protocols, imaging sequences, determine the operational status and health of system components, and so-forth.

Figure 4:
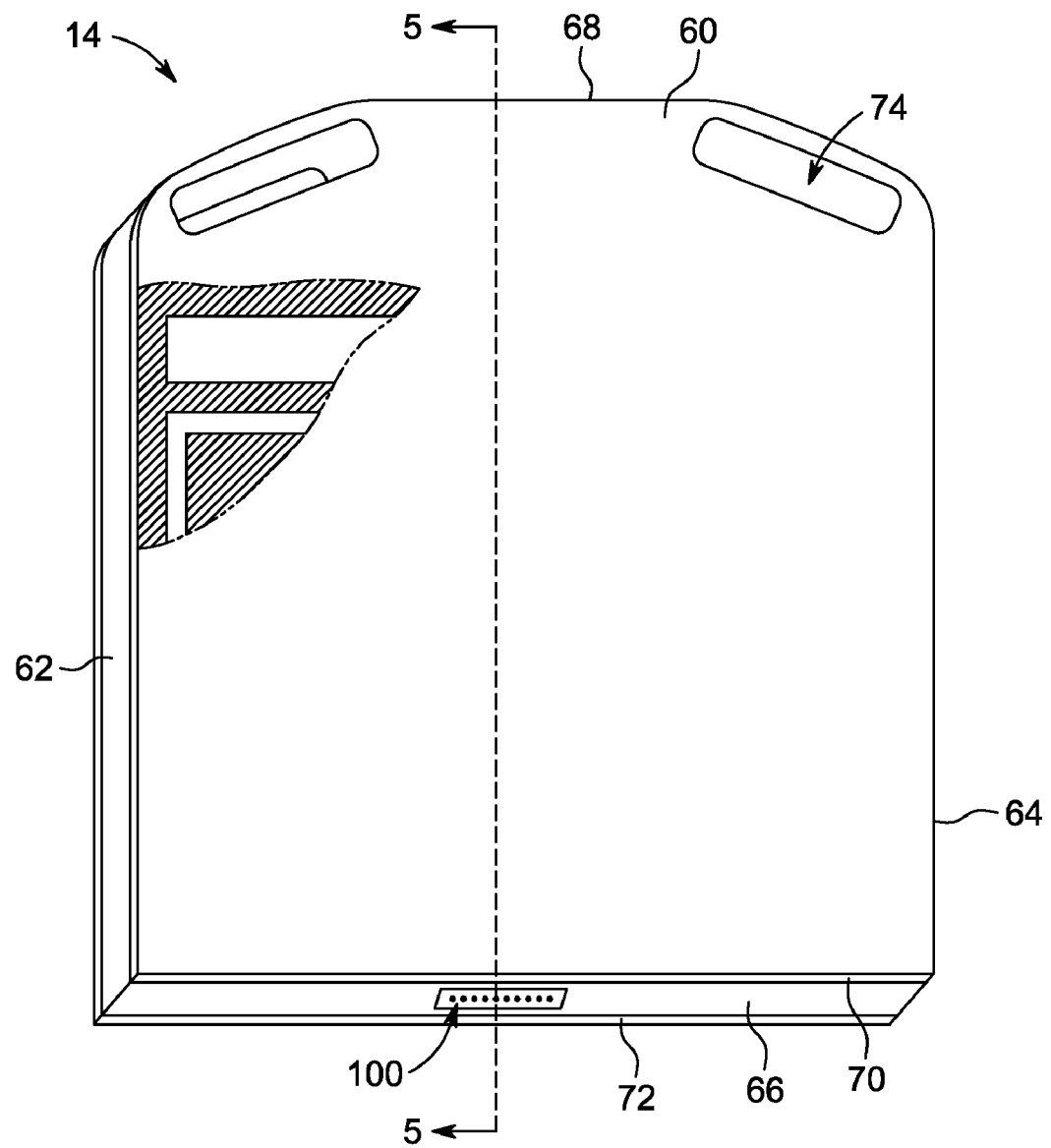
FIG. 4 is a top cut-away view of the exemplary portable x-ray detector shown in FIGS. 1, 2, and 3 in accordance with various embodiments.

FIG. 4 is a top cut-away view of the portable detector 14 shown in FIGS. 1-3. In the exemplary embodiment, the detector 14 includes a detector state monitoring system 110 (shown in FIG. 6) that is discussed in more detail below. In operation, the detector state monitoring system 110 determines when the portable detector 14 is in a portable state or a fixed state. The detector state monitoring system 110 also determines, when the detector 14 is in a portable state, whether the portable detector 14 is being operated in the digital cassette mode or being charged in the charging bin 20. Based on this determination, the detector state monitoring system 110 modifies an operational mode of the detector 14.

Referring again to FIG. 4, the detector 14 includes a casing 60. The casing 60 is formed to include a pair of sidewalls 62 and 64, a bottom side 66, and an opposing top side 68. The casing 60 also includes a front cover 70, shown as a surface parallel to the plane of the illustration, and an opposing back cover 72. The casing 60 also includes a handle 74 that extends from the front cover 70 to the back cover 72. During operation, the handle 74 enables an operator to transport the portable detector 14 from one location to another. Specifically, the handle 74 can be used to facilitate mounting, carrying and/or storing the portable detector 14. The sidewalls, top and bottom walls, the front and back covers together form the casing 60. The casing 60 may be made of a lightweight, low atomic number (N) material, such as aluminum, or a graphite material. Graphite has a lower weight than aluminum, but it is also stiffer and less energy-absorbent.

The portable detector 14 also includes a docking connector 100. The docking connector 100 is configured to mate with various other connectors. For example, the docking connector 100 is configured to mate with a charging connector 140 (shown in FIG. 7) that is installed on the charging bin 20 and a bucky connector 160 (shown in FIG. 8) that is installed on the cassette holder 22. The charging connector 140 and the bucky connector 160 are described in more detail below.

Figure 5:
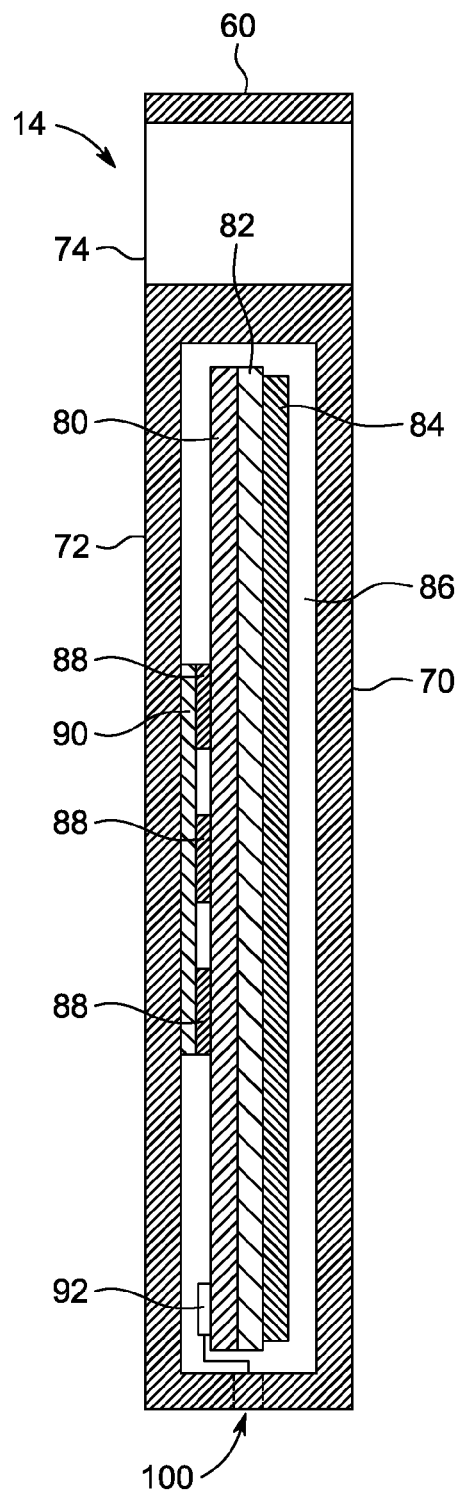
FIG. 5 is a side cut-away view of the detector shown in FIG. 4 in accordance with various embodiments.

FIG. 5 is a side cut-away view of the portable detector 14 shown in FIG. 4 viewed along the line 5-5 of FIG. 4. As shown in FIG. 5, the detector 14 also includes a circuit board 80 that is affixed to a panel support 82 that may be fabricated from a low N material, which in turn is affixed (e.g., using an adhesive) to a panel 84. The panel 84 may be a glass panel and may include X-ray scintillator material. In the exemplary embodiment, the panel 84 includes a scintillator material. As such, during operation, the panel 84 is formed to include a plurality of detector rows that each includes a plurality of detector elements (not shown), that together sense the projected X-rays that pass through an object, such as a patient. During operation, each detector element produces an electrical signal that represents the intensity of an impinging X-ray beam and hence allows estimation of the attenuation of the beam as the beam passes through the subject 18. In some embodiments, the panel support 82 is not used, and the circuit board 80 is affixed directly to the panel 84. Together, circuit board 80 and the panel 84 (and panel support 82, if present) comprise an "electronic assembly."

To provide some degree of break resistance for panel 84, a gap 86 is provided between the panel 84 and the front cover 70. Also, the electronic assembly does not physically contact any wall of the casing 60, but is mounted to the back cover 72. Additionally, heat generating components 88 on the circuit board 80 may be thermally coupled to back cover 72 using a heat conducting compound 90. The heat conducting compound 90 provides, directly or indirectly, a mechanical coupling between the circuit board 80 and the back cover 72. In the exemplary embodiment, the portable detector 14 also includes a processor 92 that is mounted to the circuit board 80. The processor 92 is configured to store information to operate the portable detector 14 and/or to transmit information to a remote location via the wireless transceiver 54 or the docking connector 100. Accordingly, in the exemplary embodiment, the docking connector 100 is electrically coupled to the processor 92 and both form a portion of the detector state monitoring system 110 which is discussed in more detail below. Specifically, the processor 92 is programmed to receive inputs from the docking connector 100, and based on the received inputs, determine when the portable detector 14 is in the fixed state or the portable state.

Figure 6:
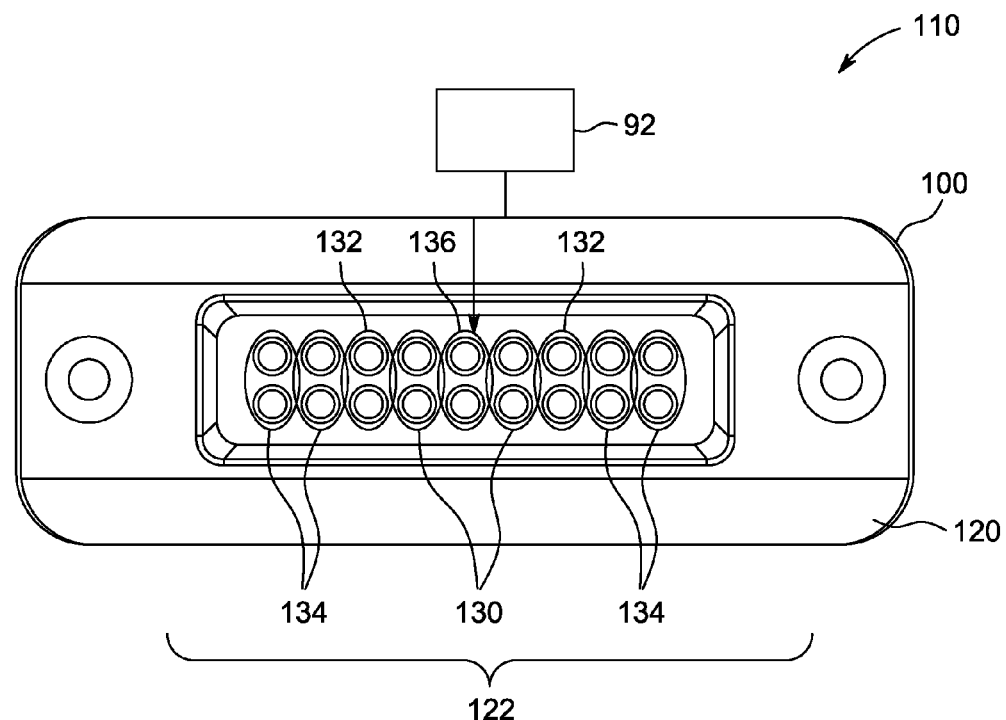
FIG. 6 is a pictorial illustration of an exemplary detector state monitoring system that may be used with the imaging system shown in FIGS. 1, 2, and 3.

FIG. 6 is a front view of the exemplary detector state monitoring system 110. The detector state monitoring system 110 includes at least the docking connector 100 and the processor 92. The processor 92 is electrically coupled to the docking connector 100. The docking connector 100 includes a connector housing 120 and a plurality of docking connector contacts or pins 122 that are installed in the connector housing 120. As discussed above, the docking connector 100 is configured to mate with the charging connector 140 that is installed on the charging bin 20 and also mate with the bucky connector 160 that is installed on the cassette holder 22. In one embodiment, the docking connector pins 122 are fabricated from a conductive tubular material to enable the docking connector pins 122 to be inserted into complementary openings of either the charging connector 140 or the bucky connector 160. In another embodiment, the docking connector pins 122 are receptacles that are configured to receive a complementary pin therein.

In the exemplary embodiment, the docking connector 100 includes a plurality of power supply pins 130. The power supply pins 130 are configured to receive power from the charging bin 20 when the detector 14 is installed in the charging bin 20. The power supply pins 130 are also configured to receive power from the cassette holder 22 when the detector 14 is installed in the cassette holder 22. In one embodiment, the docking connector 100 includes at least one power supply pin 130. In the exemplary embodiment, the docking connector 100 includes four power supply pins 130. During operation, the charging bin 20 and the cassette holder 22 are each configured provide approximately 12 volts DC to the detector 14 via the four power supply pins 130. In the exemplary embodiment, utilizing four power supply pins 130 reduces the amount of voltage drop across the mated connector. Each mated pin pair represents resistance between the source (the power supply) and the load (the detector). Using more than one pin pair decreases the total resistance.

During operation, the voltage drop across a resistor is proportional to the current (drawn by the load, the detector), therefore increasing the number of pin pairs in the mated connector decreases the resistance and therefore the voltage drop across the mated connector between the power supply and the detector. As such, each mated pin pair conducts a portion of the current drawn by the detector. For example, utilizing four pin pairs enables each mated pin pair to supply nominally $\frac{1}{4}^{th}$ of the power to the detector. Furthermore, increasing the quantity of power supply pins 130 utilized to conduct power to the portable detector 14 substantially reduces the possibility of an electrical arc occurring at the docking connector 100, when the portable detector 14 is coupled or uncoupled from either the charging bin 20 or the cassette holder 22. It should be realized that although the exemplary embodiment illustrates the docking connector 100 as including four power supply pins 130, the docking connector 100 may include fewer than four or greater than four power supply pins 130. Accordingly, in the exemplary embodiment, the docking connector 100 includes N=4 power supply pins 130.

As shown in FIG. 6, the docking connector 100 also includes a plurality of power return pins 132. The power return pins 132 are configured to provide an electrical power return pathway from the portable detector 14 back to either the charging bin 20 when the detector 14 is installed in the charging bin 20 or the cassette holder 22 when the detector 14 is installed in the cassette holder 22. In the exemplary embodiment, the docking connector 100 also includes N power return pins 132, where in the exemplary embodiment, N=4.

The docking connector 100 also includes a plurality of Ethernet pins 134 for forming one or more Ethernet ports. The Ethernet pins 134 are configured to receive and transmit information from the detector 14 to the imaging system 10 via the cassette holder 22. The docking connector 100 further includes a pair of detector state pins 136. The detector state pins 136 are utilized by the processor 92 to enable the processor 92 to determine whether the detector 14 is installed in the charging bin 20 or the cassette holder 22. The operation of the detector state pins 136 is discussed in more detail below.

Figure 7:
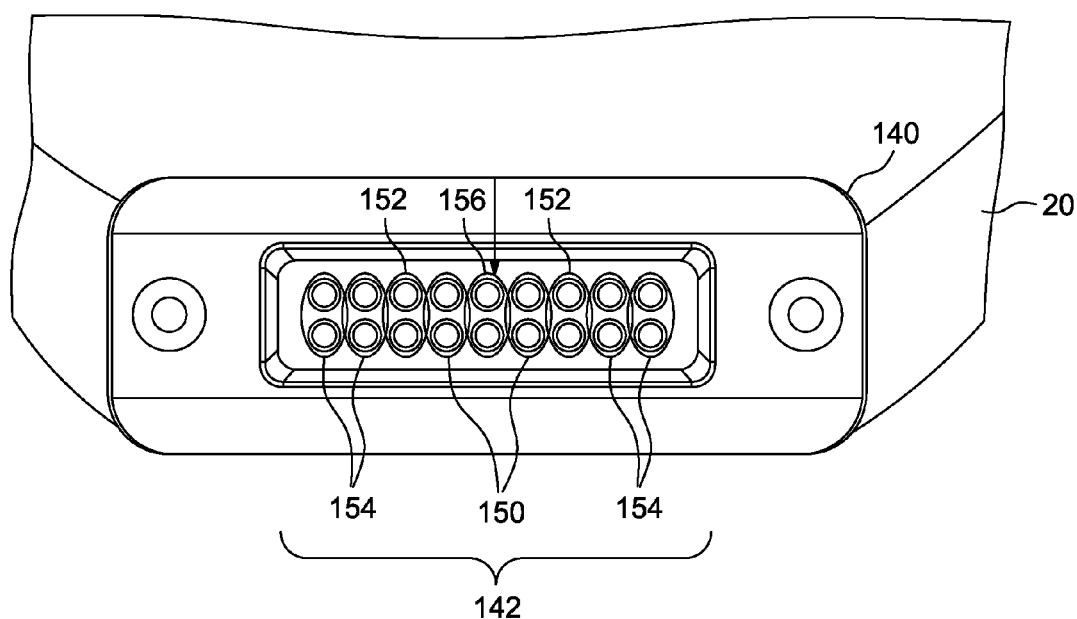
FIG. 7 is a front view of an exemplary charging connector that may be used with the detector state monitoring system shown in FIG. 6 in accordance with various embodiments.

FIG. 7 is front view of an exemplary charging connector 140 that may be installed in the charging bin 20. In the exemplary embodiment, when the portable detector 14 is installed in the charging bin 20, or coupled to the charging bin 20, the charging connector 140 is configured to mate with the docking connector 100 to enable power to be transmitted between the portable detector 14 and the charging bin 20. Accordingly the charging connector 140 is substantially similar to the docking connector 100 in size and shape to enable the charging connector 140 to mate with the docking connector 100. The charging connector 140 includes a plurality of pins 142. The pins 142 are configured to mate with the docking connector pins 122 installed on the docking connector 100. In one embodiment, the pins 142 are fabricated from a conductive tubular material to enable the pins 142 to be inserted into complementary openings of the docking connector pins 122. In another embodiment, the pins 142 are receptacles that are configured to receive a complementary docking connector pin 122 therein.

The charging connector 100 also includes a plurality of power supply pins 150. The power supply pins 150 are configured to conduct power from charging bin 20 when the detector 14 is installed in the charging bin 20 to the docking connector 100 and thus to the portable detector 14. In the exemplary embodiment, the charging connector 140 includes N power supply pins 150, wherein N=4. As discussed above, during operation approximately ¼ of the total power supplied to the portable detector 14 is conducted through each power supply pin 150 to a respective power supply pin 130 in the docking connector 100.

The charging connector 140 also includes a plurality of power return pins 152 that provide the return power pathway from the portable detector 14, via the power return pins 132, back to the charging bin 20 when the detector 14 is installed in the charging bin 20. The charging connector 140 may also include a plurality of Ethernet pins 154. The Ethernet pins 154 are configured to mate with the Ethernet pins 134 to form Ethernet ports that enable information to be transmitted and received between the detector 14 and the imaging system 10.

The charging connector 140 further includes a pair of detector state pins 156. The detector state pins 156 are used in conjunction with the detector state pins 136 to enable the processor 92 to determine whether the portable detector 14 is installed in the charging bin 20 or the cassette holder 22. The operation of the detector state pins 156 is discussed in more detail below. As shown in FIG. 7, in the exemplary embodiment, the detector state pins 156 are electrically isolated from each other such that a resistance measured across the pair of detector state pins 156 is substantially infinity.

Figure 8:
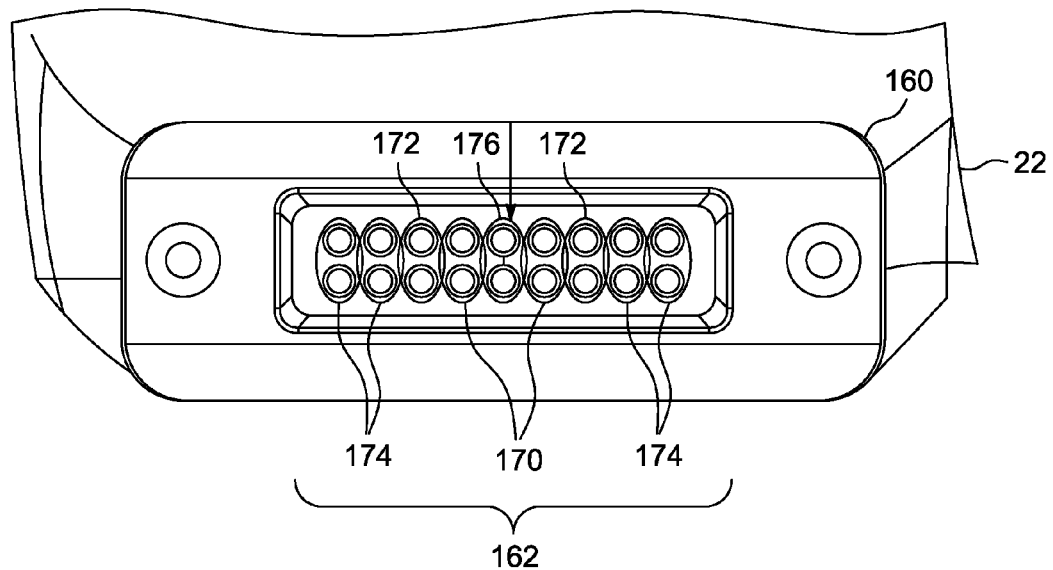
FIG. 8 is a front view of an exemplary bucky connector that may be used with the detector state monitoring system shown in FIG. 6 in accordance with various embodiments.

FIG. 8 is front view of an exemplary bucky connector 160 that may be installed in the cassette holder 22. In the exemplary embodiment, when the portable detector 14 is installed in the cassette holder 22, or coupled to the cassette holder 22, the bucky connector 160 is configured to mate with the docking connector 100 to enable power and information to be transmitted between the portable detector 14 and the cassette holder 22. Accordingly, the bucky connector 160 is substantially similar to the docking connector 100 in size and shape to enable the bucky connector 160 to mate with the docking connector 100. The bucky connector 160 includes a plurality of pins 162. The pins 162 are configured to mate with the docking connector pins 122 installed on the docking connector 100. In one embodiment, the pins 162 are fabricated from a conductive tubular material to enable the connecting pins 162 to be inserted into complementary openings of the docking connector pins 122. In another embodiment, the pins 162 are receptacles that are configured to receive a complementary docking connector pins 122 therein.

The bucky connector 160 also includes a plurality of power supply pins 170. The power supply pins 170 are configured to conduct power from cassette holder 22 when the detector 14 is installed in the cassette holder 22 to the docking connector 100 and thus to the portable detector 14. In the exemplary embodiment, the bucky connector 160 includes N power supply pins 170, wherein N=4. As discussed above, during operation approximately ¼ of the total power supplied to the portable detector 14 is conducted through each power supply pin 170 to a respective power supply pin 130 in the docking connector 100.

The bucky connector 160 also includes a plurality of power return pins 172 that provide the return power pathway from the portable detector 14, via the power return pins 132, back to the cassette holder 22 when the detector 14 is installed in the cassette holder 22. The bucky connector 160 also includes a plurality of Ethernet pins 174. The Ethernet pins 174 are configured to receive and transmit information from the detector 14 to the imaging system 10 via the Ethernet pins 134 on the docking connector 100.

The bucky connector 160 further includes a pair of detector state pins 176. The detector state pins 176 are used in conjunction with the detector state pins 136 to enable the processor 92 to determine whether the portable detector 14 is installed in the charging bin 20 or the cassette holder 22. The operation of the detector state pins 176 is discussed in more detail below. As shown in, FIG. 8, in the exemplary embodiment, the detector state pins 176 are electrically coupled together to form a short circuit. Thus, the measured resistance across the detector state pins 176 is substantially equal to zero.

Figure 9:
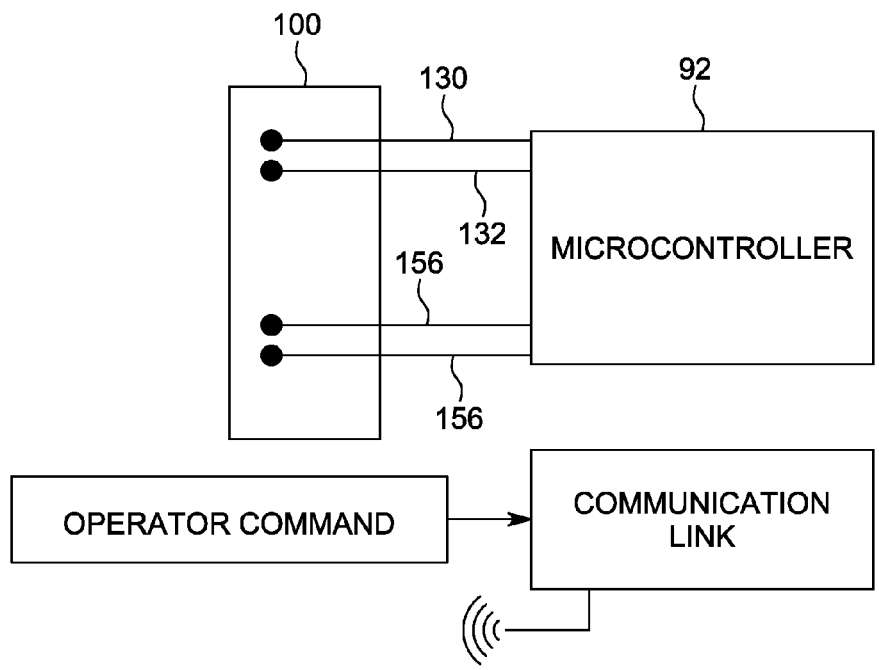
FIG. 9 is a simplified schematic illustration of the detector state monitoring system shown in FIG. 6 in accordance with various embodiments.
Figure 10:
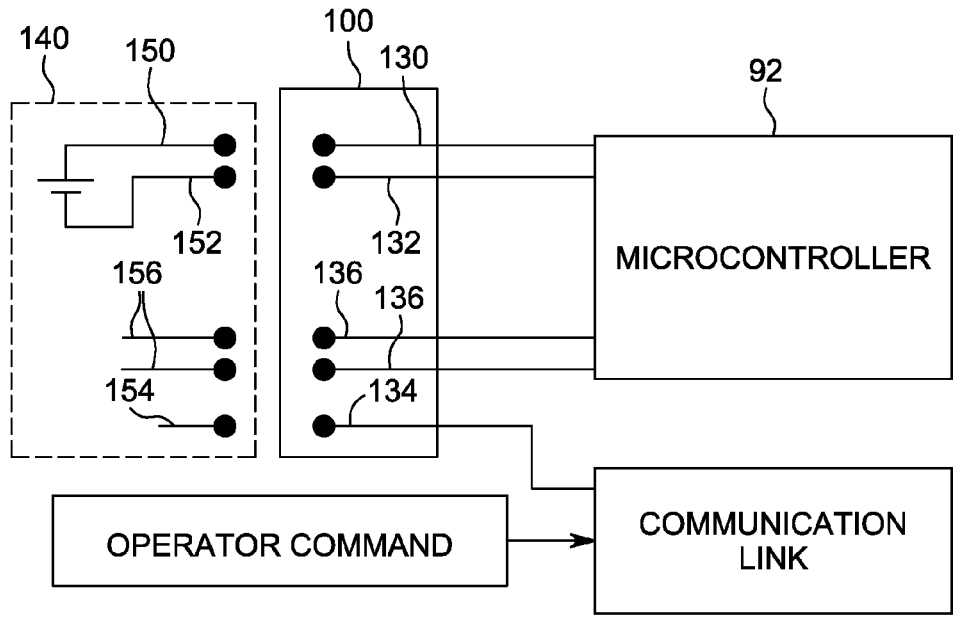
FIG. 10 is another simplified schematic illustration of the detector state monitoring system shown in FIG. 6 in accordance with various embodiments.
Figure 11:
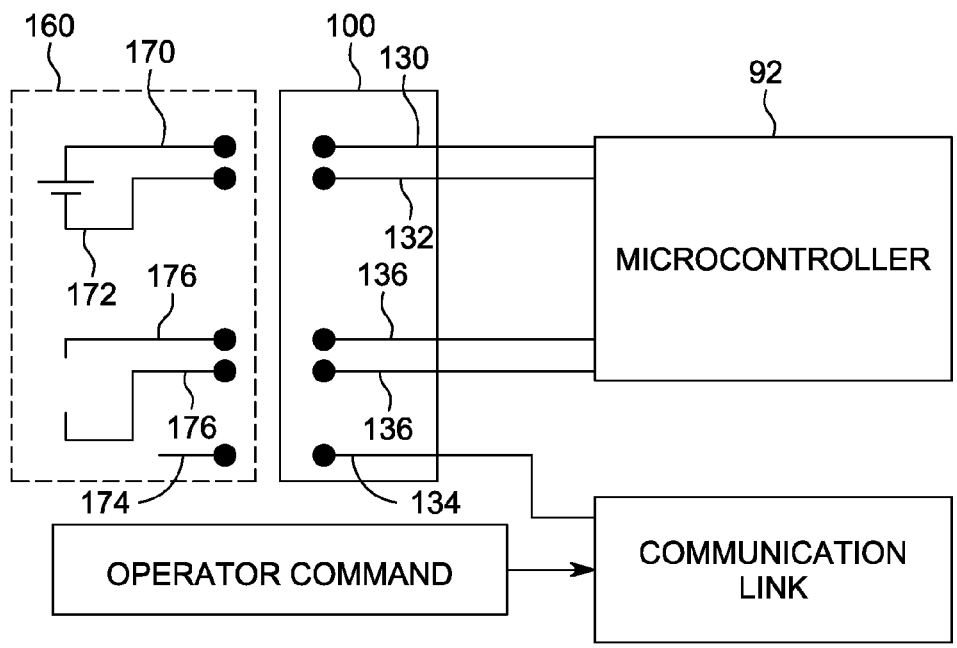
FIG. 11 is another simplified schematic illustration of the detector state monitoring system shown in FIG. 6 in accordance with various embodiments.

FIGS. 9 and 10 are simplified schematic illustrations of the detector 14 being configured in the portable state. FIG. 11 is a simplified schematic illustration of the detector 14 being configured in the fixed state. More specifically. FIG. 9 is a simplified schematic illustration of the detector 14 operating in the digital cassette mode, FIG. 10 is a simplified schematic illustration of the detector 14 coupled to the charging bin 20, and FIG. 11 is a simplified schematic illustration of the detector 14 coupled to the cassette holder 22. It should be realized that although the docking connector 100, the charging connector 140 and the bucky connector 160 include a plurality of connecting pins as discussed above, that only a portion of the pins are illustrated to explain the operation of the detector state monitoring system 110. For example, as discussed above, in the exemplary embodiment, the docking connector 100, the charging connector 140 and the bucky connector 160 each include four power pins and four return pins, however FIGS. 9, 10, and 11 illustrate only a portion of the power and return pins.

The detector 14 is configured to be operated in a portable state or a fixed state. In the portable state, the detector 14 is either operated wirelessly or is being charged. Specifically, the detector 14 is either operating in the digital cassette mode or is coupled to the charging bin 20. The detector 14 is also configured to be operated in the fixed state. In the fixed state, the detector 14 is coupled to the cassette holder 22.

During operation, the detector state monitoring system 110 first determines whether the portable detector is operating in the digital cassette mode or is installed in either the charging bin 20 or the cassette holder 22. Initially, the detector state monitoring system 110 measures a voltage across the power supply pin 130 and power return pin 132 installed in the docking connector 100. If the detector 14 is operated in the digital cassette mode, e.g. operated using the battery installed in the portable detector 14, the voltage measured between the power supply pin 130 and the power return pin 132 is approximately zero volts. However, if the detector 14 is installed in either the charging bin 20 or the cassette holder 22, the voltage measured across the power supply pin 130 and the power return pin 132 will be greater than 0 volts. As shown in FIG. 9, the detector 14 is being operated in the digital cassette mode, e.g. a portable state, therefore the measured voltage is approximately 0 volts. As shown in FIG. 10 the detector 14 is installed in the charging bin 20 and therefore the measured voltage across the power supply pin 130 and the power return pin 132 is greater than zero volts. Additionally, as shown in FIG. 11 the detector 14 is installed in the cassette holder 22 and therefore the measured voltage across the power supply pin 130 and the power return pin 132 is greater than zero volts.

The detector state monitoring system 110 therefore utilizes the voltage measured across the power supply pin 130 and the power return pin 132 to determine if the detector is operating in the digital cassette mode or is installed in either the charging bin 20 or the cassette holder 22. If the detector state monitoring system 110 determines that the detector 14 is operating in the digital cassette mode, the detector state monitoring system 110 automatically configures the detector 14 in an operational mode based on the portable state.

However, if the detector state monitoring system 110 determines that the detector 14 is installed in either the charging bin 20 or the cassette holder 22, e.g. voltage >0 is measured at the docking connector 100, the detector state monitoring system 110 utilizes the pair of detector state pins 136 to determine if the detector 14 is installed in the charging bin 20 or the cassette holder 22.

As discussed above, the pair of detector state pins 156 in the charging connector 140 are electrically isolated from each other. Moreover, the pair of detector state pins 176 in the bucky connector 160 are electrically coupled together or shorted together. Therefore, during operation, the detector state monitoring system 110 measures the resistance across the detector state pins 136 to determine if the detector 14 is installed in the charging bin 20 or the cassette holder 22. If the resistance measured across the detector state pins 136 is large i.e. greater than 100 Ohms, for example, the detector state monitoring system 110 determines that the detector 14 is installed in the charging bin 20 as shown in FIG. 10. Optionally, if the resistance measured across the detector state pins 136 is approximately 0 Ohms, the detector state monitoring system 110 determines that the portable detector 14 is installed in the cassette holder 22 as shown in FIG. 11. The detector state monitoring system 110 is then programmed to automatically configure the detector 14 in an operational mode based on whether the detector 14 is installed in the charging bin 20 or the cassette holder 22.

Figure 12:
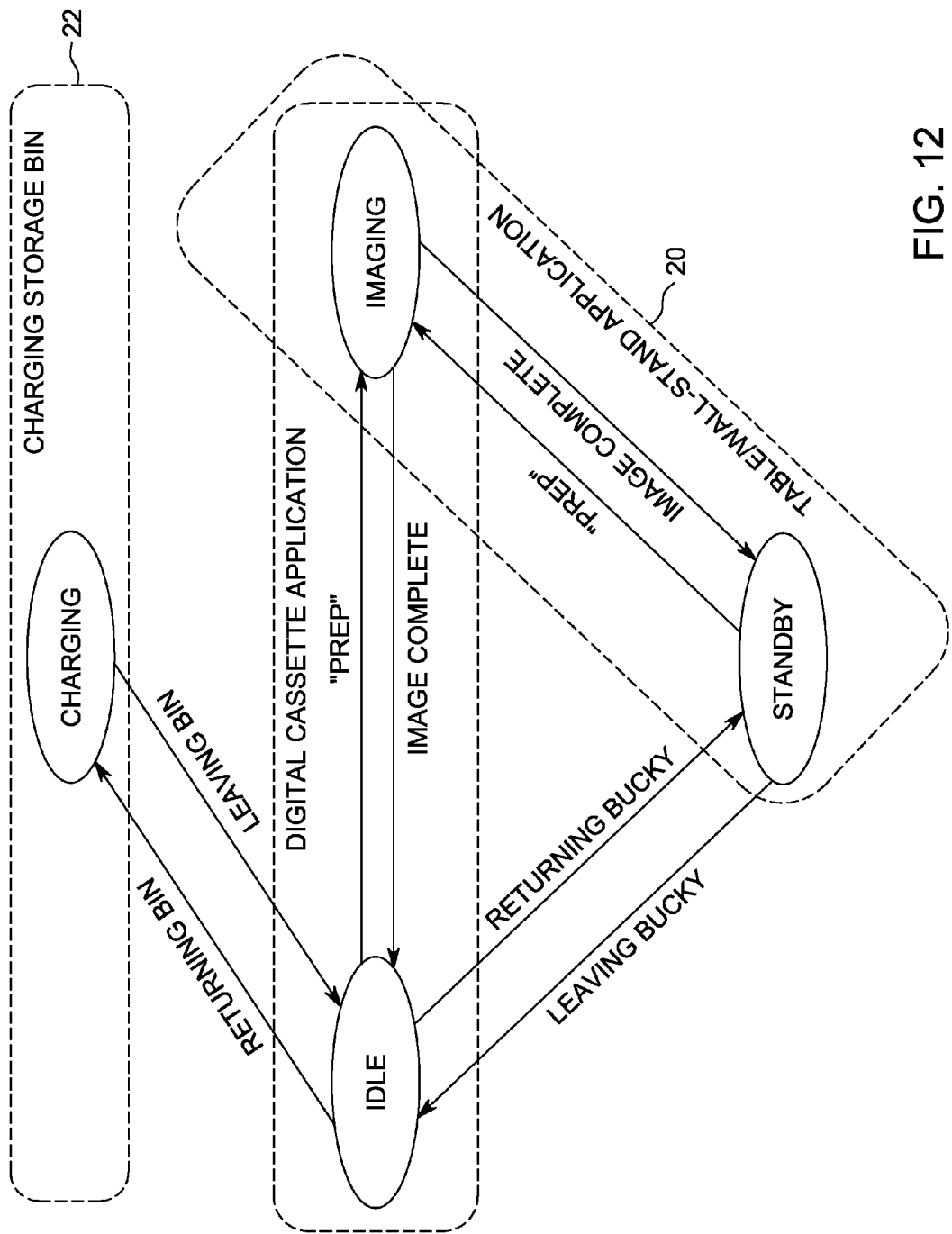
FIG. 12 is a simplified flow chart that illustrates an exemplary method of operating the detector state monitoring system shown in FIG. 6 in accordance with various embodiments.

FIG. 12 is a simplified flowchart illustrating various operational modes that may be implemented by the detector state monitoring system 110. More specifically, the detector state monitoring system 110 enables the portable detector 14 to operate in a plurality of operational modes. The operational modes may include for example, a detector sleep or idle mode. In the detector idle mode, power is conserved by deactivating at least some of the components within the detector 14 that consume the majority of power. Additionally, other remaining components, e.g. the detector state monitoring system 110, for example, remain activated to enable the operator to operate the detector 14 and thus to configure the detector 14 in other modes as discussed below. When the operator does something that causes the detector to "wake up", such as insert the detector 14 into the cassette holder 22, the detector 14 is configured to transition from the "idle mode" to a "standby" mode. In the standby mode, power from an external supply (i.e. other than the battery) is supplied to the detector state monitoring system 110, the transceiver 54, and the detector electronics. e.g. the panel 84. In the active mode, the detector 14 is configured to communicate with a remote station, such as the workstation 30. In some operational modes, only a portion of the detector elements on the panel 84 may be activated to perform imaging. In the imaging mode, the detector 14 is operational to acquire scanning information as discussed above. In the charging mode, the detector 14 is almost completely deactivated.

It should be realized that the detector 14 is configured to operate in a plurality of operational modes. Moreover, the power consumed by the detector 14 may be different in each operational mode. For example, in the idle mode, the detector 14 consumes relatively little power. Whereas, in the standby mode, the detector 14 consumes more power than in the idle mode. Additionally, in the imaging mode, the detector 14 consumes the most power.

Referring again to FIG. 12, when the portable detector 14 is installed in the charging bin 20. e.g. in a portable state, and the portable detector 14 is removed from the charging bin 20 and used wirelessly in the digital cassette mode, the detector state monitoring system 110 automatically transitions the portable detector 14 from the charging mode to the idle mode. To transition from the idle mode to the imaging mode, the operator merely depresses a button (not shown) to initiate imaging. The button may be installed on the portable detector 14 or located remotely from the portable detector 14. If the detector 14 is reinstalled in the charging bin 20, the detector state monitoring system 110 automatically transitions the portable detector 14 from the idle mode back to the charging mode.

If the portable detector 14 is transitioned from the portable state to a fixed state, for example by installing the portable detector into the cassette holder 22, the detector state monitoring system 110 automatically transitions the portable detector 14 from the idle mode to the standby mode. To transition from the standby mode to the imaging mode, the operator merely depresses the button to initiate imaging. After imaging is completed, the detector state monitoring system 110 automatically transitions the portable detector 14 from the imaging mode back to the standby mode. When the portable detector 14 is removed from the cassette holder 22, the detector state monitoring system 110 automatically transitions the portable detector 14 from the standby mode back to the idle mode.

A technical effect of the various embodiments is to determine whether the portable detector is operating in a portable state or a fixed state and then to automatically operate the portable detector in a predetermined operational mode based on the identified state. Described herein is a portable and wireless x-ray detector that includes a detector state monitoring system. The detector communicates with an x-ray system via a wireless device when operated in a portable state, e.g. in a digital cassette application. The detector communicates with the x-ray system via a docking connector when operated in a fixed state application. The detector is powered by its internal battery in digital cassette mode and by an external power source through the docking connector in a table and/or wall-stand in the fixed state. Optionally, the detector 14 may be installed in a charging bin. In the fixed state, the detector communicates with the imaging system using a gigabit Ethernet connection. In the portable state, the detector 14 communicates with the imaging system wirelessly. Optionally, in the portable state, the detector 14 may communicate with the imaging system via a tether.

Accordingly, the portable detector described herein is configured to operate in a relatively low power consumption state when operating in the portable state to enable the detector to operate over an extended time while simultaneously conserving power in the battery, thus enabling the detector to operate longer on a single battery charge. Moreover, the portable detector includes both a wireless and wired connection to the x-ray system which supports high performance advanced applications.

In some embodiments, the docking connector installed on the detector includes a plurality of metallic conductors that are substantially flat on the pad plane for the ease of cleaning. During operation, the detector determines whether it is in digital cassette mode by sensing the absence of external power on the docking connector. A plurality of power conductors are utilized to reduce the current flowing through each pin of the connector to reduce or eliminate an electric arc from occurring when the detector is connected and disconnected from the charging bin or the cassette holder. The plurality of pins reduces potential arcs which may damage the pins and also increases the reliability of the connector by eliminating failure due to a single contact fault.

The detector also distinguishes when the external power is present. If external power is present, the detector is either in the charging bin or cassette holder. The detector further distinguishes the charging bin from the cassette holder by measuring the resistance across the two conductors in the docking connector. The corresponding two conductors on the x-ray system end are designed with different resistance for the charging bin and the cassette holder. Further, the portable detector may be tested while the portable detector is physically installed in the cassette holder. Testing is particularly appealing for mobile detectors because a detector self test can be performed by removing the charging power just after the operator starts the portable x-ray system to drive the unit to patient rooms. Identifying problems prior to removing the detector from the bin in preparation for an exam is preferable over having the system notify the operator to replace the detector battery after positioning has been completed, for example.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose various embodiments of the invention, including the best mode, and also to enable any person skilled in the art to practice the various embodiments, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of operating a portable imaging detector, the portable imaging detector including a docking connector having a first pair of docking connector contacts, said method comprising:

measuring a voltage across the first pair of docking connector contacts; and determining whether the portable detector is (i) operating in a digital cassette mode or is (ii) installed in either a cassette holder or a charging bin using the measured voltage.

2. A method in accordance with claim 1 further comprising measuring a resistance across a second pair of docking connector contacts to determine if the portable detector is installed in either the cassette holder or the charging bin.

3. A method in accordance with claim 2 further comprising automatically placing the portable detector in a first mode when the portable detector is determined to be installed in the cassette holder.

4. A method in accordance with claim 2 further comprising automatically placing the portable detector in a second mode when the portable detector is determined to be installed in the charging bin.

5. A method in accordance with claim 2 further comprising:
configuring the portable detector in a first operational state when the measured resistance across the second pair of docking connector contacts is less than a threshold value, and
configuring the portable detector in a second different operational state when the measured resistance across the second pair of docking connector contacts is greater than a threshold value.

6. A method in accordance with claim 1 wherein the docking connector includes a plurality of power contacts, said method further comprising measuring a voltage across at least two of the plurality of power contacts.

7. A method in accordance with claim 1 further comprising transitioning the portable detector from a second mode to a third mode when the portable detector is removed from the charging bin.

8. A method in accordance with claim 1 further comprising transitioning the portable detector from a third mode to a first mode when the portable detector is placed in the cassette holder.

9. A detector state monitoring system comprising:
a docking connector coupled to a portable imaging detector, the docking connector having a first pair of docking connector contacts; and
a processor coupled to the docking connector, the processor programmed to:
determine when the portable detector is (i) operating in a digital cassette mode or is (ii) installed in either a cassette holder or a charging bin based on a voltage measured across the first pair of contacts.

10. A detector state monitoring system in accordance with claim 9 wherein the processor is further programmed to use the measured voltage to determine if the portable detector is being operated independently from its own battery while in the digital cassette mode.

11. A detector state monitoring system in accordance with claim 9 wherein the processor is further programmed to automatically place the portable detector in a second mode when the portable detector is determined to be installed in the charging bin.

12. A detector state monitoring system in accordance with claim 9 wherein the processor is further programmed automatically place the portable detector in a first mode when the portable detector is determined to be installed in the cassette holder.

13. A detector state monitoring system in accordance with claim 9 wherein the processor is further programmed to:
configure the portable detector in a first operational state when the measured resistance across a second pair of docking connector contacts is less than a threshold value, and
configure the portable detector in a second different operational state when the measured resistance across the second pair of docking connector contacts is greater than a threshold value.

14. A detector state monitoring system in accordance with claim 9 wherein the docking connector includes a plurality of power contacts, the detector state monitoring system further programmed to measure a voltage at the plurality of power contacts.

15. A detector state monitoring system in accordance with claim 9 wherein the processor is further programmed to:
transition the portable detector from a second mode to a third mode when the portable detector is removed from the charging bin; and
transition the portable detector from a third mode to a first mode when the portable detector is installed into the cassette holder.

16. A portable X-ray detector comprising:
a detector panel; and
a detector state monitoring system coupled to the detector panel, the detector state monitoring system including a docking connector having a first pair of docking connector contacts, and a processor coupled to the docking connector, the processor programmed to:
determine when the portable detector is (i) operating in a digital cassette mode or is (ii) installed in either a cassette holder or a charging bin based on a voltage measured across the first pair of contacts.

17. A portable X-ray detector in accordance with claim 16 wherein the detector state monitoring system is further configured to measure a resistance at a second docking connector contact to determine if the portable detector is installed in either the cassette holder or the charging bin.

18. A portable X-ray detector comprising:
a detector panel including a first pair of docking connector contacts; and
a processor coupled to the first pair of docking connector contacts, the detector panel wirelessly transmitting information to a remote location when the portable detector is operating in a portable state of operation, and transmitting information over a cable to a remote location when the portable detector is operating in a fixed state of operation, the processor programmed to determine when the portable detector is (i) operating in a digital cassette mode or is (ii) installed in either a cassette holder or a charging bin based on a voltage measured across the first pair of docking connector contacts.

19. A portable X-ray detector in accordance with claim 18 wherein the detector
transitions from a second mode to a third mode when the portable detector is removed from the charging bin, and
transitions from a third mode to a first mode when the portable detector is installed a cassette the cassette holder.

* * * * *